US012770251B2

(12) United States Patent
Arnal et al.

(10) Patent No.: US 12,770,251 B2
(45) Date of Patent: Oct. 20, 2026

(54) QUANTATIVE ANALYSIS OF FLUCTUATIONS IN BIOLOGICAL TISSUES VIA MULTISPECTRAL PHOTOACOUSTIC IMAGING

(71) Applicants: UNIVERSITÉ GRENOBLE ALPES, Saint Martin d'Heres (FR); CENTRE NATIONAL DE LA RECHERCHE SCIENTIFIQUE, Paris (FR)

(72) Inventors: Bastien Arnal, Grenoble (FR); Emmanuel Bossy, Corenc (FR); Guillaume Godefroy, Brunoy (FR)

(73) Assignees: UNIVERSITÉ GRENOBLE ALPES, Saint Martin d'Heres (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 296 days.

(21) Appl. No.: 18/292,135

(22) PCT Filed: Jul. 20, 2022

(86) PCT No.: PCT/FR2022/051444
§ 371 (c)(1),
(2) Date: Jan. 25, 2024

(87) PCT Pub. No.: WO2023/012416
PCT Pub. Date: Feb. 9, 2023

(65) Prior Publication Data

US 2024/0346645 A1 Oct. 17, 2024

(30) Foreign Application Priority Data

Aug. 3, 2021 (FR) ...................................... 2108452

(51) Int. Cl.
*G06T 5/70* (2024.01)
*A61B 5/00* (2006.01)
(Continued)

(52) U.S. Cl.
CPC .......... *G06T 7/0012* (2013.01); *A61B 5/0095* (2013.01); *A61B 5/14542* (2013.01);
(Continued)

(58) Field of Classification Search
CPC ..................... G06T 7/0012; G06T 5/70; G06T 2207/10016; G06T 2207/10132;
(Continued)

(56) References Cited

U.S. PATENT DOCUMENTS

2013/0016284 A1* 1/2013 Mestha ..................... G06T 5/50 348/E5.062

FOREIGN PATENT DOCUMENTS

CN 103826524 A * 5/2014 ....... A61B 1/000094
CN 111481172 A * 8/2020 ........... A61B 5/4848

OTHER PUBLICATIONS

Photoacoustic fluctuation imaging: theory and application to blood flow imaging (Year: 2020).*
A unified framework for photoacoustic fluctuation imaging. Application to visibility enhancement with fluctuations induced by blood flow. (Year: 2017).*
Enhancement of in vivo cardiac photoacoustic signal specificity using spatiotemporal singular value decomposition (Year: 2021).*
(Continued)

*Primary Examiner* — Huo Long Chen
(74) *Attorney, Agent, or Firm* — NIXON & VANDERHYE

(57) ABSTRACT

A method is disclosed for processing photoacoustic images, this method including: obtaining a time series of images of a sample, the images being acquired by a photoacoustic imaging system at Mx excitation-pulse wavelengths, with N images acquired per wavelength; performing multispectral spatio-temporal filtering via singular value decomposition applied to all of the N*Mx acquired images so as to obtain N*Mx filtered images; for each wavelength, computing a filtered variance image based on the N filtered images, a pixel of coordinate r in the filtered variance image being equal to the variance of the distribution of the values of pixels of same coordinate r in the filtered images obtained
(Continued)

for this wavelength; and correcting the filtered variance image by subtracting a variance of the residual electronic noise after the multispectral spatio-temporal filtering has been performed, the noise being produced by the sensors of ultrasonic waves of the photoacoustic imaging system.

10 Claims, 8 Drawing Sheets

(51) Int. Cl.
*A61B 5/145* (2006.01)
*G06T 7/00* (2017.01)

(52) U.S. Cl.
CPC ...... *G06T 5/70* (2024.01); *G06T 2207/10016* (2013.01); *G06T 2207/10132* (2013.01); *G06T 2207/30101* (2013.01)

(58) Field of Classification Search
CPC ........ G06T 2207/30101; A61B 5/0095; A61B 5/14542; A61B 5/725; A61B 5/7217; A61B 2576/00
See application file for complete search history.

(56) References Cited

OTHER PUBLICATIONS

Sergey Vilov et al, "Photoacoustic fluctuation imaging: theory and application to blood 1-11 flow imaging" , arxiy.org, Cornell University Library, Nov. 18, 2020, XP081816499, 21 pages.
Sergey Vilov et al, "A unified framework for photoacoustic fluctuation imaging. 1-11 Application to visibility enhancement with fluctuations induced by blood flow", arxiy.org, Cornell University Library, Jun. 16, 2020, XP081707980, 20 pages.
Hill Emma R. et al, "Identification and removal of laser-induced noise in photoacoustic imaging using singular value decomposition", Biomedical Optics Express, vol. 8, No. 1, Jan. 1, 2017, Retrieved from the Internet: https://www.ncbi.nlm.nih.gov/pmc/articles/PMC52313 16/pdf/68.pdf , 10 pages.
Al Mukaddim Rashid et al., "Enhancement of in vivo cardiac photoacoustic signal specificity using spatiotemporal singular value decomposition" Journal of Biomedical Optics, vol. 26, No. 4, Apr. 1, 2021, retrieved on Apr. 19, 2021, 19 pages.
International Search Report for PCT/FR2022/051444, mailed Nov. 8, 2022, 4 pages.
Written Opinion of the ISA for PCT/FR2022/051444, mailed Nov. 8, 2022, 8 pages.
Search Report for FR2108452, dated May 23, 2022, 4 pages.
Written Opinion for FR2108452, dated Aug. 3, 2021, 9 pages.

* cited by examiner $$A(r,t) = \sum_{k=1}^{N \times M_\lambda} S_k \, U_k(r) V_k(t)^* \xrightarrow{330} A_{SVD}(r,t) = \sum_{k=a}^{b} S_k \, U_k(r) V_k(t)^*$$

QUANTATIVE ANALYSIS OF FLUCTUATIONS IN BIOLOGICAL TISSUES VIA MULTISPECTRAL PHOTOACOUSTIC IMAGING

This application is the U.S. national phase of International Application No. PCT/FR2022/051444 filed Jul. 20, 2022, which designated the U.S. and claims priority to FR Patent Application No. 2108452 filed Aug. 3, 2021, the entire contents of each of which are hereby incorporated by reference.

TECHNICAL FIELD

The present document relates to acoustic resolution photoacoustic imaging and more precisely to a method of processing images acquired by a multispectral photoacoustic imaging system and an associated device.

TECHNOLOGICAL BACKGROUND

The technique of photoacoustic imaging (also called opto-acoustic) is based on the generation of ultrasonic waves produced in a sample (typically, a biological tissue) by excitation by irradiating the sample with electromagnetic radiation, typically laser pulses within the spectrum from 300 to 2000 nm, especially in the window of 650 to 950 nm.

In general, a photoacoustic image is reconstructed from the measurement of acoustic signals generated by absorption of the light sent on the sample. For reasons related to the efficiency of photoacoustic generation, short nanosecond pulses are generally used for biomedical imaging for illuminating the biological tissue to be imaged: the absorption of the pulsed light creates a rapid rise in temperature in the soft tissue which generates by thermoelastic effect a rise in pressure, which pressure then relaxes by causing the propagation of pulsed acoustic waves in the biological tissue.

Acoustic resolution photoacoustic imaging differs from optical resolution photoacoustic imaging in that an array of ultrasonic wave sensors is used: knowing the speed of sound, an image indicating the amplitudes and positions of sound sources can be reconstructed from the received acoustic signals. Whereas in optical resolution photoacoustic imaging each light pulse is focused point by point on the surface of the sample, and the sound emitted from the optical focal zone is measured by a single ultrasonic wave sensor.

Acoustic resolution photoacoustic imaging is a biomedical imaging technique that provides in depth optical absorption contrast in biological tissues. Photoacoustic imaging of blood e.g. is used for imaging blood vessels. Blood, via hemoglobin, is indeed a very abundant absorbing element in the human body.

However, fixed photoacoustic imaging devices using piezoelectric sensor arrays to capture ultrasonic waves have visibility limits and certain tissue structures do not appear on the acquired images due to the limitations of sensors in terms of bandwidth and numerical aperture, when the sensor array does not encompass the imaged medium. The use of acquisition systems with limited numerical aperture and limited bandwidth thus causes artifacts of limited visibility: the vessels the axes of which are almost aligned with the axis of the probe are invisible as well as large size vessels. More particularly, waves received on and around the 90° side are not accessible and only approximately horizontal vascular structures are detected, but vertical structures do not appear.

To solve such problem, it is possible to use a tomographic approach and use broadband detectors. Such non-resonant detectors do not, however, allow ultrasound imaging to be performed and the associated tomographic approaches are not compatible with all clinical and preclinical problems.

Approaches based on artificial intelligence with deep learning have also been proposed recently, for overcoming visibility problems but such solution raises problems of availability of training data as well as of generalization.

There is thus a need for a better adapted biological tissue imaging solution.

SUMMARY

According to a first aspect, a method of processing photoacoustic images comprises: obtaining a temporal succession of images of a sample acquired by a photoacoustic imaging system for Mx excitation pulse wavelengths with N images acquired per wavelength; a multispectral spatio-temporal filtering by singular value decomposition applied to all the $N*M_\lambda$ images acquired so as to obtain $N*M_\lambda$ filtered images; for each wavelength, a calculation of a filtered variance image from the N filtered images, one pixel of coordinate r in the filtered variance image being equal to the variance of the distribution of pixel values of the same coordinate r in the filtered images obtained for said wavelength; for each wavelength, a correction of the filtered variance image by subtracting a variance of the residual electronic noise after multispectral spatio-temporal filtering produced by ultrasonic wave sensors of the photoacoustic imaging system. The corrected variance image thus obtained is proportional at each image point to the square of the energy absorbed at a point in space corresponding to the image point concerned.

In one or a plurality of embodiments, the method comprises, for each wavelength, a determination of a corrected image of fluctuations, each pixel of which is equal to the square root of the corresponding pixel of the corrected variance image obtained by said subtraction for the wavelength considered. The corrected image of fluctuations thus obtained is proportional in each image point to the energy absorbed at a point of the space corresponding to the image point concerned.

In one or a plurality of embodiments, the method further comprises an estimation of the variance of the residual electronic noise produced by the ultrasonic wave sensors on the images, the variance of the residual electronic noise produced by the ultrasonic wave sensors on the images being estimated as a function of a variance of the electronic noise produced in the photoacoustic signals acquired in the absence of a sample corrected by an amount of noise eliminated by multispectral spatio-temporal filtering by decomposition into singular values, the amount of noise eliminated being estimated based on the singular values corresponding to the lowest energy components removed by the multispectral spatio-temporal filtering by singular value decomposition.

In one or a plurality of embodiments, the method comprises, for each wavelength considered, a normalization of the image of fluctuations corrected by a function of the laser pulse fluence of the photoacoustic imaging system, so as to obtain an image of absorption fluctuations representative of the absorption fluctuations due to the sample.

In one or a plurality of embodiments, multispectral spatio-temporal filtering by singular value decomposition comprises a selection of the components corresponding to the highest energy singular values to be removed and removing selected components, the selection being made by choosing from a set of index values, an index identifying the first component to be kept for which a contrast-to-noise ratio is maximum, the contrast-to-noise ratio determined for an index being calculated from filtered variance images calculated by multispectral spatio-temporal filtering by decomposition into singular values applying the index.

In one or a plurality of embodiments, the contrast-to-noise ratio is determined by eliminating the contrast due to the mean value of the acquired images for at least one wavelength.

In one or a plurality of embodiments, the method comprises a calculation of an oxygen saturation rate image from at least two images of absorption fluctuations obtained for at least two corresponding wavelengths. The calculation can be performed on the basis of a model expressing, for each pixel of the coordinate r, a relation between a total hemoglobin concentration, an oxygen saturation level and the value at the pixel r of the image of absorption fluctuations.

According to another aspect, a photoacoustic image processing device comprises at least one data storage comprising program code instructions, at least one data processor, the data processor being configured to, when the program code instructions are executed by the data processor, make the photoacoustic image processing device execute a photoacoustic image processing method according to any of the embodiments.

In another aspect, a computer-readable data storage comprises computer program instructions that, when executed by a processor, execute a photoacoustic image processing method according to any of the embodiments.

According to another aspect, a computer program comprising computer program instructions that, when executed by a processor, execute a photoacoustic image processing method according to any of the embodiments.

BRIEF DESCRIPTION OF FIGURES

Other features and advantages will result from the detailed description which follows, made on the basis of embodiments and examples given as an illustration, and not in a limiting way, with reference to the enclosed figures wherein.

DETAILED DESCRIPTION

Figure 1:
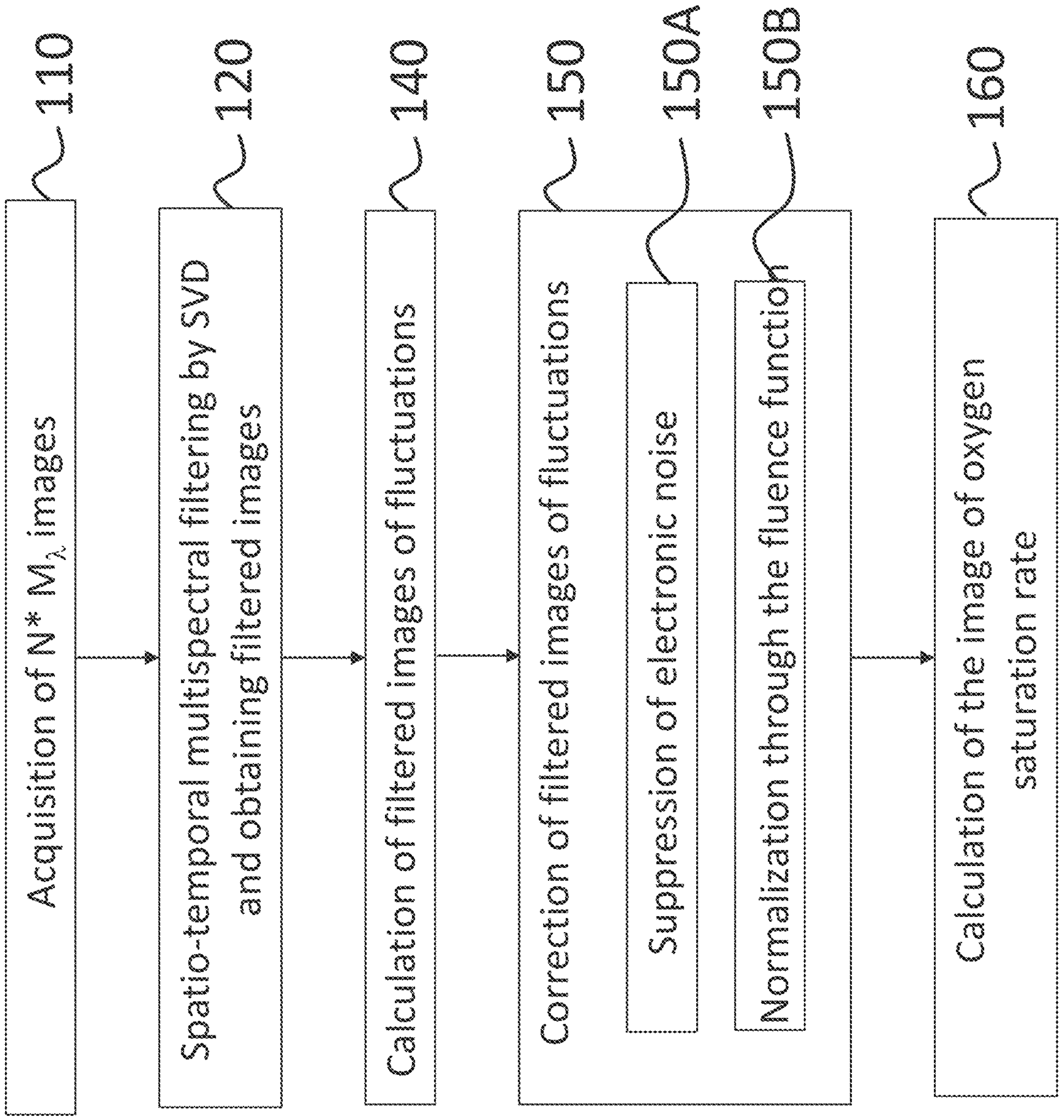
FIG. 1 represents a simplified flow chart of a method for processing images acquired by a multispectral photoacoustic imaging system.

A method for processing images acquired by a multispectral photoacoustic imaging system using an array of acoustic wave sensors for the acquisition of ultrasonic waves produced in a sample to be imaged (generally a biological tissue) by laser excitation, will be described in more detail.

The method is applicable to photoacoustic imaging of any type of fluctuations occurring in biological tissues. The application of the method to the quantitative analysis of the blood oxygenation rate will be described as a non-limiting example.

Within the framework of the present document, image of fluctuations refers to an image representative of temporal fluctuations at each image point, each image point (or pixel) representing a standard deviation of the fluctuations considered. An image of fluctuations can thus be obtained from a temporal succession of images, each pixel of coordinate r in the image of fluctuations being calculated from the standard deviation of the statistical distribution of the pixels of the same coordinate r in the temporal succession of images. To each image of fluctuations corresponds a variance image, designating the image of fluctuations squared: each image point of the variance image representing a variance of the fluctuations considered, i.e. a variance of the statistical distribution of pixels of the same coordinate in the temporal succession of images considered. Depending on the context, we will talk about the variance image or the image of fluctuations.

Within the framework of the present document, the images can be 2D or 3D images. For simplicity, the term "image pixel" or "image point" will be used herein in general to refer to a picture element. A pixel or image point corresponds to a voxel in the case of a 3D image. The image processing method uses a multispectral quantitative analysis of the fluctuations detected for a given sample voxel from the different images acquired. Images (usually 3D images) of fluctuations representing, at each pixel, the fluctuations of the pixel values representing a given voxel of the biological tissue, are thus generated for each wavelength. For example, at each pixel describing a blood vessel, the blood flow causes an amplitude fluctuation from one image to another. More particularly, in the case of blood vessels, red blood cells do not have exactly the same spatial conformation from image to image, which modulates local absorption over time. Like standard photoacoustic imaging, it is possible to show (see e.g. the document entitled "Photoacoustic fluctuation imaging: theory and application to blood flow imaging", by Vilov S., Godefroy G., Arnal B., & Bossy E.; Optica, 7(11), 1495-1505 (2020)) that under ideal conditions (without noise and spurious fluctuations, at constant hematocrit), the photoacoustic image of fluctuations is proportional to the product of the local optical absorption $u_\lambda(r)$ multiplied by the fluence of the laser pulse $\phi_\lambda(r)$:

$$\sigma\left[A_{k,\lambda}^{ideal}\right](r) = A \cdot \phi_\lambda \; (r) \cdot \mu_\lambda(r) \qquad \text{[Math. 01]}$$

where r is a vector identifying a spatial position in an acquired three-dimensional (3D) image, A is a constant that does not depend on λ or r if one can consider a spatial invariance of the point spread function of the ultrasonic imager. If the point spread function varies in space, then the dependence of A on r can be taken into account and corrected.

For each wavelength of a plurality of wavelengths, an image of fluctuations can be determined. This image of fluctuations is representative of temporal fluctuations due to biological tissue (e.g., due to blood flow) but is affected by the pulse-to-pulse fluctuation of the laser and by the electronic noise of the ultrasonic wave sensors.

Indeed, apart from fluctuations in biological tissue, there are other sources of spurious fluctuations: fluctuations in the energy of laser pulses and electronic noise produced in particular by the ultrasonic wave sensors of the multispectral photoacoustic imaging system. It is thereby necessary to carry out a specific processing so that the image of fluctuations is representative only (or mainly) of the fluctuations of interest: herein, the fluctuations of the absorption due to the biological sample. The image of fluctuations obtained by the method described in the present document is in fact proportional to the absorption of the chromophores of the biological sample responsible for the absorption fluctuations. Such an image will be referred to as "image of absorption fluctuations".

Thereby, due to fluctuations in laser pulse energy, the image of fluctuations, even if obtained by subtracting the average photoacoustic image, always comprises a residual term corresponding to the average photoacoustic image multiplied by the variance of the pulse energy. Multispectral spatio-temporal filtering by Singular Value Decomposition (SVD) effectively eliminates the residual term due to the specific spatio-temporal signature thereof. In general, by removing the components of the image corresponding to the first singular values, not only fluctuations in laser pulse energy are removed, possible movements (e.g. physiological) occurring in the biological sample, but also the contribution due to the average absorbing element in the image and only the parts of the image corresponding to temporal fluctuations of interest are kept. Furthermore, it appears that SVD has better performance when performed on a set of multispectral images than when applied on images having the same wavelength.

Filtered images of fluctuations are then generated for each wavelength from a temporal succession of filtered images obtained at the end of the multispectral spatio-temporal filtering. In the filtered image of fluctuations at a given wavelength, a pixel of coordinate r in the image of fluctuations is equal to the standard deviation of the distribution of pixel values of the same coordinate r in the filtered images obtained for said wavelength.

It is also possible to perform a correction of the filtered image of fluctuations obtained for each wavelength so as to keep only the fluctuations of interest and obtain a corresponding image of fluctuations of interest or image of variance of interest.

A first type of correction consists in correcting fluctuations due to the electronic noise of ultrasonic wave sensors. Such correction allows the image of fluctuations to become proportional to $\phi_\lambda(r)\mu_\lambda(r)$. The noise being additive in the space of variances, the step could consist in estimating the background noise in the image space resulting from the electronic noise picked up by the ultrasonic wave sensors and subtracting same from each pixel of the variance image, so as to obtain a corrected variance image the square root of which, the corrected image of fluctuations, is representative at each pixel only of the fluctuation due to the biological tissue considered in the corresponding voxel of the sample (in the example, by blood flow), weighted by the distribution of fluence. The corrected image of fluctuations is thereby proportional at each image point to the energy absorbed at a point in the space corresponding to the image point concerned.

A second type of correction consists in normalizing by a fluence function, the corrected image of fluctuations obtained after correcting the fluctuations due to the electronic noise of the ultrasonic wave sensors.

The raw, unfiltered variance image obtained from the raw images which are not filtered by SVD for a given wavelength, corresponds at each pixel, to the sum of the variance representing the fluctuations induced in the corresponding voxel of the sample (in the example, the fluctuations induced by a blood flow), weighted by the fluence of the pulse, and of the variance of the electronic noise of ultrasonic wave sensors in the image space.

Mathematically, it can be shown that:

$$\sigma^2[A_{i,\lambda}(r)] = \mathrm{var}_i[A_{i,\lambda}(r)] = \phi_\lambda^2(r)\left(1+\sigma_{\phi,\lambda}^2\right)\sigma_{\lambda,flow}^2(r) + \sigma_{\phi,\lambda}^2|m_\lambda(r)|^2 + \sigma_b^2 \quad \text{[Math. 10]}$$

where $$\sigma^2[A_{i,\lambda}(r)] \quad \text{[Math. 11]}$$

is the value of the pixel of coordinates r in the raw variance image obtained from the raw images acquired (not filtered by SVD) for the wavelength λ calculated on the realizations indexed by i, the realizations corresponding to the temporal succession of the images acquired for the wavelength λ;

$$\phi_\lambda^2(r) \quad \text{[Math. 12]}$$

is the mean square fluence of the laser for the wavelength λ at the pixel of coordinates r;

$$\sigma_{\phi,\lambda}^2 \quad \text{[Math. 13]}$$

is the variance of the relative fluctuation of the laser pulse to pulse energy for the wavelength λ (referred to as "pulse energy fluctuation", PEF);

$$|m_\lambda(r)|^2 \quad \text{[Math. 14]}$$

is the modulus squared of the value of the pixel of coordinates r in the mean image $m_\lambda$ calculated as the mean of the images $A_{i,\lambda}(r)$ acquired at the wavelength λ;

$$\sigma_{\lambda,flow}^2(r) \quad \text{[Math. 15]}$$

is the value of the pixel of coordinates r in the image of variance of interest and represents the temporal fluctuations due to biological tissue in a given voxel corresponding to the pixel of coordinate r, normalized by:

$$\phi_\lambda^2(r) \quad \text{[Math. 16]}$$

$$\sigma_b^2 \quad \text{[Math. 17]}$$

is the variance of electronic noise due to ultrasonic wave sensors in the image.

We can see that the PEF term influences two terms: same biases the coefficient on the variance image and is a prefactor of the mean image. Since the mean image is one to two orders of magnitude greater than the fluctuation due to biological tissue, a correction is necessary to recover the variance image of interest even if the PEF is low.

Monitoring the PEF by means of a photodiode at the output of the laser can also be an insufficient correction method because of the spatial fluctuations of the laser beam that the photodiode cannot measure. The SVD method eliminates the effects of PEF in order to obtain complete filtered images. The elimination of the first singular values during multispectral spatio-temporal filtering by the SVD has the effect of removing the contributions of the average absorber subjected to the PEF. SVD filtering also changes the background level of the variance image. Thus, after multispectral spatio-temporal filtering by the SVD, a filtered variance image is obtained, corresponding to the filtered image of fluctuations, such as:

$$\sigma^2\left[A_{i,\lambda}^{SVD}(r)\right] = \phi_\lambda^2(r)\left(1+\sigma_{\phi,\lambda}^2\right)\sigma_{\lambda,flow}^2(r) + \sigma_{b,SVD}^2 \quad \text{[Math. 20]}$$

where $$\sigma_{b,SVD}^2 \quad \text{[Math. 21]}$$

is the variance of residual electronic noise after SVD filtering;

$$\sigma_{\phi,\lambda}^2 \quad \text{[Math. 22]}$$

is the variance of the relative fluctuation (variance normalized by the square of the mean value) of laser pulse energies at the wavelength λ.

The relative fluctuation of laser pulses is usually a few percent and can be neglected.

Indeed, $$\sigma_{\phi,\lambda} \sim 10^{-2} \quad \text{[Math. 23]}$$

and $$\sigma_{\phi,\lambda}^2 \sim 10^{-4} \quad \text{[Math. 24]}$$

So one can write $$\sigma^2\left[A_{i,\lambda}^{SVD}(r)\right] = \phi_\lambda^2(r)\sigma_{\lambda,flow}^2(r) + \sigma_{b,SVD}^2 \quad \text{[Math. 25]}$$

Hence:

$$\sigma\left[A_{k,\lambda}^{ideal}\right](r) = \phi_\lambda(r)\sigma_{\lambda,flow}(r) = \sqrt{\sigma^2\left[A_{i,\lambda}^{SVD}(r)\right] - \sigma_{b,SVD}^2} \quad \text{[Math. 26]}$$

Thereby, it can be seen that an image of absorption fluctuations $\sigma_{\lambda,flow}(r)$ representative of the absorption fluctuations of the biological tissue can be obtained by applying two corrections successively.

The first correction consists in subtracting, at each pixel of the filtered variance image, the variance of the residual electronic noise after filtering by SVD in order to obtain a corrected variance image and then a corresponding corrected image of fluctuations by taking the square root.

The second correction consists in normalizing the image of fluctuations corrected by the fluence of the laser pulse $\phi_\lambda(r)$, by dividing each pixel by $\phi_\lambda(r)$ so as to obtain a corrected and normalized image of fluctuations, called image of absorption fluctuations $\sigma_{\lambda,flow}(r)$ or image of fluctuations of interest. The two corrections are applied for each wavelength considered.

The images of absorption fluctuations $\sigma_{\lambda,flow}(r)$ thereby obtained for each excitation wavelength are representative only (or at least mainly) of the absorption fluctuations induced by the biological tissue. In the case where the absorption fluctuations in the biological tissue are mainly those due to the blood flow, $\sigma_{\lambda,flow}(r)$ represents the absorption fluctuations due to the blood flow.

An approach of fluctuations by imaging can thereby be used for solving the problems of visibility mentioned in the introduction, as well as for improving the contrast, at the cost of acquiring a series of images. For example, information on fluctuations within large size vessels and information on vertically oriented vessels can be obtained.

Such method is useful in particular in the case of image acquisition by means of fixed acquisition devices held by hand (called "handheld devices" or "single-sided devices") or held by a mechanical part, which are placed on the skin of the subject in order to image a given region, without the need for movement during the acquisition. In such acquisition devices, the acoustic wave sensors are e.g. piezoelectric sensors with limited visibility (limited passband and angular reception spectrum).

Furthermore, a quantitative analysis of the blood oxygenation rate is possible. Indeed, in the case of the application to imaging of oxygenation of blood vessels, from the different images of absorption fluctuations obtained for different wavelengths, 2D or 3D oxygenation maps can be determined by inverting a model linking the fluctuation maps due to blood flow at different wavelengths normalized by the fluence, to the rate of oxygenation. A quantification of the optical absorption spectra of blood vessels can be achieved therefrom. More precisely, using tissue excitation light waves at a plurality of wavelengths, the relative or absolute amount of oxyhemoglobin and deoxyhemoglobin can be determined from the differences in absorption profile obtained according to the wavelength.

To obtain an oxygenation map, it is possible to start either from images of fluctuations corrected and normalized by the incident fluence in the case where there is no spectral coloration due to the tissue, or from images of absorption fluctuations which are images of fluctuations corrected and normalized by the spatial fluence within the sample. In the first case, at each point there is proportionality with the images of absorption fluctuations but the attenuation of the light in depth is not corrected (which is assumed to be the same for each wavelength when there is no spectral coloration due to the tissue).

Quantitative imaging of the rate of oxygenation of blood vessels is thereby obtained. The image of absorption fluctuations is specific to blood flows, providing specificity in quantitative evaluations, in particular when under-resolved vessels surrounded by other absorbers are involved, and avoids the complexity of spectral unmixing. The method is particularly applicable to tumor imaging, brain imaging and vascular imaging. As mentioned hereinabove, the image of fluctuations has a better contrast than the conventional image and is not affected by the visibility artifacts present in conventional imaging. The oxygenation rate is thus obtained on an image much richer than the conventional image.

FIG. 1 shows a simplified flowchart of a method for processing images acquired by a multispectral photoacoustic imaging system.

During a step 110, a temporal succession of images is acquired by a photoacoustic imaging system for $M_\lambda$ wavelengths, i.e. N images per wavelength and $N*M_\lambda$ images in total. The acquired images are denoted by $A_{i,j}$ where i is an integer comprised between 1 and N, which represents the index of the acquired image for a given wavelength; j is an integer comprised between 1 and $M_\lambda$ and represents the index identifying the wavelength concerned. A pixel of an image $A_{i,j}$ is denoted by $A_{i,j}(r)$ where r is the coordinate of a pixel of the image.

The acquisition rate is fixed, e.g. at 100 Hz. Typically, e.g. $M_\lambda=6$ wavelengths and N=250 images per wavelength are used. More generally, N can be comprised between 10 and 100,000, $M_\lambda$ between 2 and 100, and the acquisition frequency can be comprised between 10 and 100,000 Hz.

The acquisition can be done e.g. by cyclically varying the wavelength from one image to the next: an image with a first wavelength $\lambda_1$, then an image with a second wavelength $\lambda_2$, and so on until the last wavelength $\lambda_M$, then repeating N times the same acquisition cycle with the wavelengths $\lambda_1$ to $\lambda_M$. In this way, the period between two acquisitions at the same wavelength is fixed and identical regardless of the wavelength. In the case where only two wavelengths are used, the first wavelength $\lambda_1$ is alternated with the second wavelength $\lambda_2$.

The acquired images $A_{ij}$ are subjected to a post-processing comprising the steps 120 to 150 defined hereinbelow.

During a step 120, a multispectral spatio-temporal filtering by Singular Value Decomposition (SVD) is applied to all $N*M_\lambda$ images and $N*M_\lambda$ filtered images are obtained at the end of the step, denoted by $$A_{i,j}^{SVD} \quad \text{[Math. 27]}$$

Such multispectral spatio-temporal filtering by SVD is used for effectively removing, in the variance image, the components of the average absorber, in particular the term $$\sigma_{\phi,\lambda}^2|m_\lambda(r)|^2 \quad \text{[Math. 28]}$$

resulting from fluctuations in the pulse energy of the laser and the mean image, which by the amplitude thereof, masks the fluctuations of interest. The use of SVD filtering for a plurality of wavelengths makes SVD statistically more efficient and provides components representing fluctuations of the tissue in response to a plurality of excitation wavelengths. If spatio-temporal filtering by SVD were to be used on images acquired for a single wavelength, the choice of SVD filtering limits would vary from one wavelength to another, which would make the procedure cumbersome.

During a step 140, for each wavelength separately, a filtered image of fluctuations (a filtered variance image, respectively) is determined: the standard deviation (the variance, respectively) of the distribution of pixel values of the same coordinate r in the N filtered images obtained during the step 120 for said wavelength, is calculated for obtaining the pixel of coordinate r in the filtered image of fluctuations (in a filtered variance image, respectively). Thereby, for each wavelength j, at the end of step 140, $M_\lambda$ variance images are obtained, denoted by $$\sigma_j^2[A_{i,j}^{SVD}] \quad \text{[Math. 30]}$$

or more simply $$\sigma_j^2 \quad \text{[Math. 31]}$$

With the above notation, $$\sigma_j^2[A_{i,j}^{SVD}] \quad \text{[Math. 32]}$$

where $$\sigma_j^2(r) \quad \text{[Math. 33]}$$

is the variance of the distribution of values $$\sigma_j^2[A_{i,j}^{SVD}] \quad \text{[Math. 34]}$$

at the pixel of coordinate r calculated on the realizations i=1 to N for the wavelength j. During a step 150, a correction of each filtered image of fluctuations is performed so as to obtain an image of absorption fluctuations representative, solely or essentially, of the absorption fluctuations of the biological sample. The correction of the filtered image of fluctuations thereby comprises a removal of fluctuations other than fluctuations of interest due to the sample, so as to obtain an image of absorption fluctuations representing absorption fluctuations due to the sample. Two types of corrections can be used in combination or individually.

A first type of correction (step 150A) consists in a correction of fluctuations due to the electronic noise of ultrasonic wave sensors by subtracting, at each pixel of coordinate r in the filtered variance image, the variance of the residual electronic noise after SVD, the variance of the residual electronic noise after SVD being denoted by:

$$\sigma_{b,SVD}^2 \quad \text{[Math. 35]}$$

i.e.

$$\phi_\lambda^2(r)\sigma_{\lambda,flow}^2(r) = \sigma^2\left[A_{i,\lambda}^{SVD}(r)\right] - \sigma_{b,SVD}^2 \quad \text{[Math. 36]}$$

The variance of the residual electronic noise of the acquisition sensors is estimated and then the variance $$\sigma_{b,SVD}^2$$

of the residual electronic noise is subtracted at each pixel of the filtered variance image obtained during the step 140, so as to obtain a corrected variance image for a given wavelength. The variance of the residual electronic noise after SVD can correspond to the variance of the electronic noise before SVD if the limit b of the SVD filtering is equal to the total number of images.

A corresponding corrected image of fluctuations can be obtained by calculating the square root of the corrected variance image.

The corrected image of fluctuations can then be weighted by the fluence at the wavelength considered. The corrected image of fluctuations is proportional in each image point to the energy absorbed at a point in the space corresponding to the image point concerned.

The electronic noise produced by the ultrasonic wave sensors can be estimated as a function of a variance of the electronic noise produced in the photoacoustic signals acquired in the absence of a sample, the variance being corrected by an amount of noise eliminated by multispectral spatio-temporal filtering by decomposition into singular values, wherein the amount of noise can be estimated based on singular values corresponding to the lowest energy components removed by multispectral spatio-temporal filtering by decomposition into singular values.

A second type of correction (step 150B) consists of a normalization by a function of the fluence of laser pulses at the wavelength considered. A variance image normalized by the fluence can be obtained for each wavelength by normalization by the fluence spatial function squared:

$$\phi_\lambda^2(r) \quad \text{[Math. 37]}$$

For each wavelength j=1 at $M_\lambda$ so as to obtain a normalized variance image $$\sigma^2_{\lambda,flow}(r) \quad \text{[Math. 38]}$$

representative only of absorption fluctuations produced by the sample (e.g. by the blood flow), so that:

$$\sigma^2_{\lambda,flow}(r) \quad \text{[Math. 39]}$$

represents the pixel value of the normalized variance image obtained for the wavelength λ at the pixel of the coordinate r.

The normalization by fluence can be performed on the corrected variance image using the squared fluence function $$\phi_\lambda^2(r)$$

so as to obtain a normalized variance image and then a corresponding normalized image of fluctuations by calculating the square root of each pixel. Alternatively, and equivalently, the normalization by fluence can be performed on the image of fluctuations corresponding to the corrected variance image:

$$\phi_\lambda(r)\sigma_{\lambda,flow}(r) = \sqrt{\sigma^2\left[A_{i,\lambda}^{SVD}(r)\right] - \sigma^2_{b,SVD}} \quad \text{[Math. 40]}$$

by calculating the square root of each pixel of the corrected variance image obtained after electronic noise correction before normalizing by the fluence of the laser pulse $\phi_\lambda(r)$.

Following such normalization, a normalized image of fluctuations is finally obtained, which is the image of absorption fluctuations $\sigma_{\lambda,flow}(r)$ representing the absorption fluctuations due to the sample.

With regard to the determination of the fluence function to be used for normalization, different methods and approximations are possible.

Instead of using a spatial function of the fluence, an average fluence (independent of the point in space) at a given wavelength can be used. The average fluence at a wavelength can be determined, e.g. on the basis of energy measurements of excitation pulses obtained by means of a photodiode placed at the output of the laser at the moment when an excitation pulse at a given wavelength is sent to the sample. The intensities of the electrical signals produced by the photodiode are converted into an estimation of fluence using calibration coefficients, the estimation of the fluence being used for calculating an average fluence and then performing the correction by normalization.

The fluence spatial function can be defined as follows:

$$\phi_\lambda(r) = \phi_\lambda(0)\xi_\lambda(r) \quad \text{[Math. 41]}$$

Where $$\phi_\lambda(0) \quad \text{[Math. 42]}$$

is the fluence measured at the surface of the sample, that can be obtained by a calibrated photodiode and $$\xi_\lambda(r) \quad \text{[Math. 43]}$$

represents the relative spatial variation of the fluence.

In the general case, an estimation of the spatial distribution of fluence can be obtained by modeling or by measurements.

In some cases, it can be approximated that there is no spectral coloration due to the tissue. In such case, one can write:

$$\xi_\lambda(r) = \xi(r) \quad \text{[Math. 44]}$$

In such case, an estimation of oxygenation can be made simply from the normalization by the fluence of the photodiode because the same constant:

$$\xi(r) \quad \text{[Math. 45]}$$

can be used for all wavelengths.

When the fluence is spatially uniform (chicken embryo hypothesis), the fluence can also be estimated directly from the signals produced by the photodiode, i.e.:

$$\phi_\lambda(r) = \phi_\lambda(0) \quad \text{[Math. 49]}$$

During a step 160, an image α (r) of the oxygen saturation rate is determined from at least two images of absorption fluctuations $\sigma_{\lambda,flow}$ obtained at the end of the step 150, for at least two wavelengths λ. In an alternative, the step 160 can also be executed from at least two corrected images of fluctuations $\sigma_\lambda$ (with the corrections according to the step 150A but without the corrections according to step 150B) obtained by calculating the square root of each pixel of the corresponding images of variance, obtained at the end of the step 140.

The example case is described where step 160 is executed on the basis of the images of absorption fluctuations $\sigma_{\lambda,flow}$ obtained at the end of the step 150 (the same calculations being usable starting from the corrected images of fluctuations which have not undergone the corrections according to step 150B). For this purpose, for each pixel of coordinates r, a model is used, expressing the relation between the value:

$$\sigma_{\lambda,flow}(r) \quad \text{[Math. 50]}$$

at pixel r of the image of absorption fluctuations and two parameters, K(r), including the total hemoglobin concentration and a sensitivity coefficient of the electronic receiver systems and the oxygen saturation rate α(r).

The model consists e.g. of an equation with two unknowns K(r) and α(r) giving the fluctuation:

$$\sigma_{\lambda,flow}(r) \quad \text{[Math. 51]}$$

as a function of K(r) and α(r), where r is the coordinate of an image pixel. It is thus possible to determine, for each pixel of coordinate r, the oxygen saturation level α(r) and thus generate an image α comprising, for each pixel, quantitative information on the oxygen saturation (between 0% and 100%). It is likewise possible to generate an image K comprising, for each pixel, quantitative information proportional to the total hemoglobin concentration K(r), also called "blood volume".

In one embodiment, the model is an analytical model based on the following equation:

$$\sigma_{\lambda,flow}(r) = K(r)\big(\alpha(r)\mu_{\lambda,HbO_2} + (1-\alpha(r))\mu_{\lambda,Hbb}\big) \quad \text{[Math. 52]}$$

wherein $$\mu_{\lambda,HbO_2} \quad \text{[Math. 53]}$$

is the absorption coefficient of oxyhemoglobin at the wavelength λ and $$\mu_{\lambda,Hbb} \quad \text{[Math. 54]}$$

is the absorption coefficient of desoxy-hemoglobin at the wavelength λ;

K(r) is a pre-factor that depends on the position r, but not on the wavelength λ.

Figure 2:
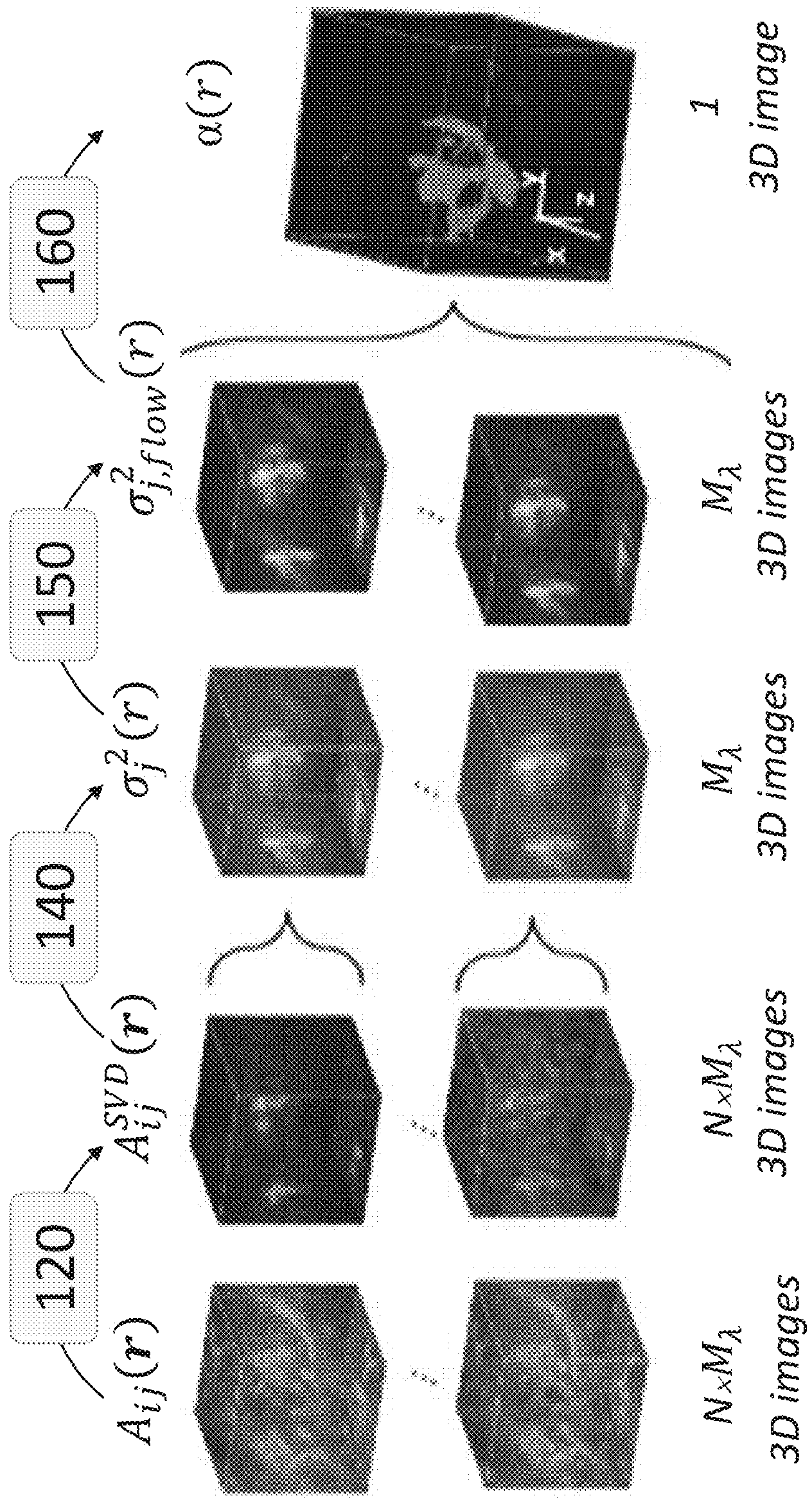
FIG. 2 illustrates aspects of a method for processing images acquired by a multispectral photoacoustic imaging system.

FIG. 2 illustrates aspects of the steps 120 to 160 based on examples of images obtained at each step.

The acquired images $A_{ij}$ obtained as input are, in the present example, three-dimensional (3D) images. We therefore have $N*M_\lambda$ acquired 3D images denoted by $$A_{1,1} \quad \text{[Math. 60]}$$

to $$A_{N,M_\lambda} \quad \text{[Math. 61]}$$

At the end of step 120 (SVD), we have $N*M_\lambda$ filtered 3D images denoted by $$A^{SVD}_{1,1} \quad \text{[Math. 62]}$$

to $$A^{SVD}_{N,M_\lambda} \quad \text{[Math. 63]}$$

At the end of the step 140 (calculation of the image of the variance), one has Mx 3D images of fluctuations, denoted by $$\sigma^2_{\lambda_1} \quad \text{[Math. 64]}$$

to $$\sigma^2_{\lambda_M} \quad \text{[Math. 65]}$$

for wavelengths $j=\lambda_1$ to $\lambda_M$. At the end of the step 150 (noise correction and/or normalization by the fluence), one has $M_\lambda$ 3D variance images representing the absorption fluctuations denoted by $$\sigma^2_{1,flow}(r) \quad \text{[Math. 66]}$$

to $$\sigma^2_{M_\lambda,flow}(r) \quad \text{[Math. 67]}$$

for wavelengths $j=\lambda_1$ to $\lambda_M$. Finally, at the end of the step 160 (calculation of the oxygen saturation), a 3D image of the oxygen saturation level is obtained, denoted by α(r).

FIG. 2 makes it possible to observe, on an example case, the effects of the different processings on the different 3D images. By comparing the acquired images with the corresponding images filtered after SVD following step 120, it is observed that only the points of the images corresponding to fluctuations of the flow are preserved. By comparing the filtered images after SVD following step 120 with the filtered image of fluctuations obtained following the step 140, we observe that certain structures appear in the filtered image of fluctuations. By comparing the filtered image of fluctuations obtained following the step 140 with the images of absorption fluctuations obtained following the step 150, it is observed that the background level is reduced to zero. Finally, it is observed that following the step 160, a volume image of the oxygen saturation level is obtained.

Figure 3A:
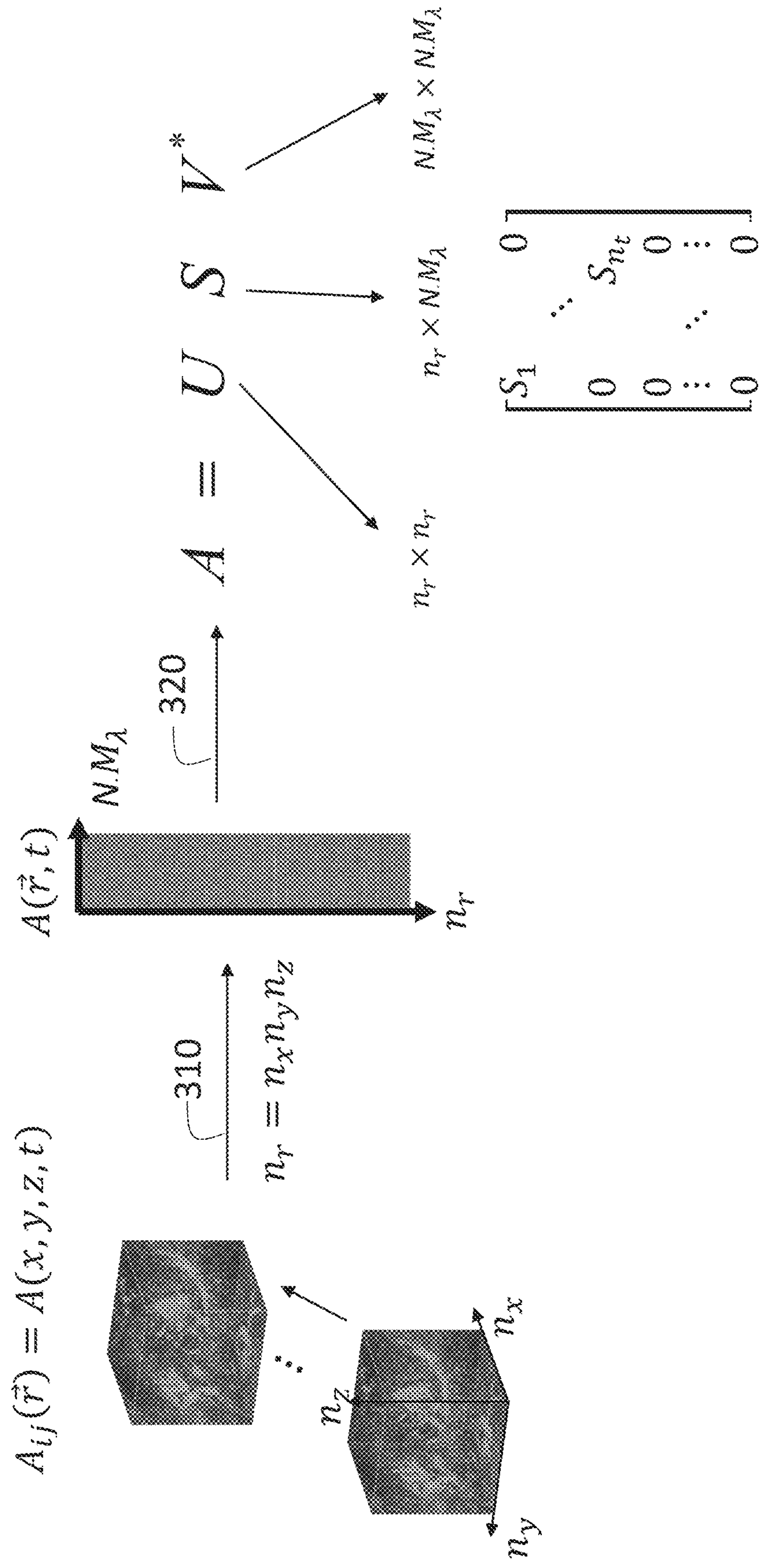
FIG. 3A illustrates aspects of a multispectral spatio-temporal filtering method by singular value decomposition that can be used in a method for processing images acquired by a multispectral photoacoustic imaging system.
Figure 3B:
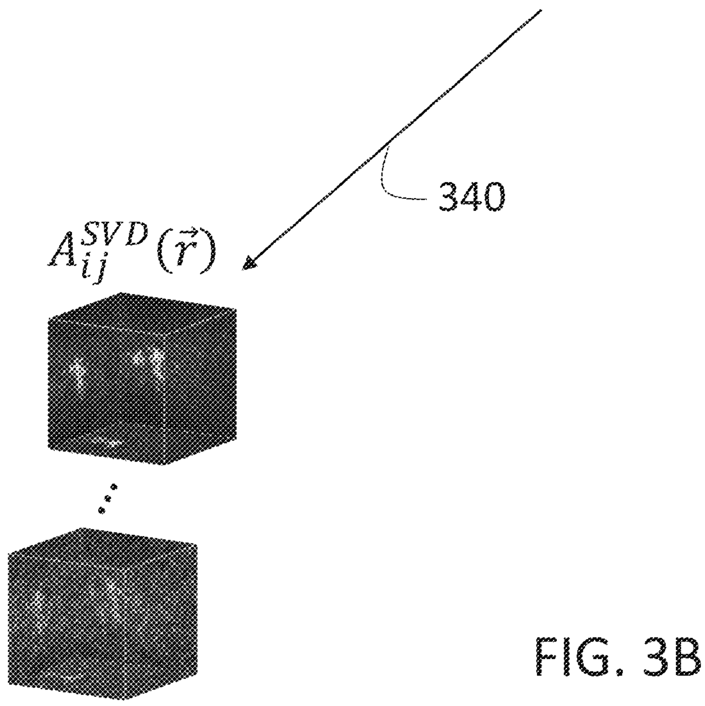
FIG. 3B illustrates aspects of a multispectral spatio-temporal filtering method by singular value decomposition that can be used in a method for processing images acquired by a multispectral photoacoustic imaging system.

FIGS. 3A-3B illustrate a multispectral spatio-temporal filtering method by SVD that can be used for the step 120 according to an exemplary embodiment.

According to what is illustrated in FIG. 3A, a temporal succession of multispectral images (1000) is acquired by a photoacoustic imaging system for $M_\lambda$ wavelengths, i.e. N images per wavelength and $N*M_\lambda$ images in total. The acquired images $A_{i,j}$ obtained as input are 3D images assumed to have identical size $n_X*n_Y*n_Z$: the number of pixels is $n_X$ along a first X axis of a 3D Cartesian space, $n_Y$ along a second Y axis and $n_Z$ along a third Z axis.

From the temporal succession of multispectral images, a two-dimensional (2D) Casorati matrix (301) is formed during a step 310, representing space and time, denoted by A(r,t), where t is a temporal index and r is a scalar corresponding to a position of a pixel in the 3D space wherein the $N*M_\lambda$ images are defined. The Casorati matrix (301) is of size $n_R*(N*M_\lambda)$, with $n_R=n_X*n_Y*n_Z$. The Casorati matrix (301) contains the pixels of the $N*M_\lambda$ images. The value t of the temporal index can thereby vary from t=1 to $N*M_\lambda$ such that $A(r,1)=A_{1,1}(r)$ is the first image of the temporal succession for a first wavelength, $A(r,2)=A_{1,2}(r)$ is the second image of the temporal succession for a second wavelength, and so on. It should be noted that in the notation A(r,1), r is a scalar while in the notation $A_{i,j}(r)$, r is a vector of coordinates (x,y,z) in a three-dimensional space. The scalar r can be calculated from the coordinates of the vector r=(x,y,z) and the size $n_X*n_Y*n_Z$ of the acquired images. The use of the Casorati matrix (301) makes it possible to perform the analysis of fluctuations in the spatio-temporal domain.

During a step 320, the Casorati matrix (301) is decomposed according to a singular value decomposition method: A=U S V* where U is a 2D matrix of size $n_R*n_R$ comprising the spatial singular vectors, S is the 2D matrix of the singular values of size $n_R*(N*M_\lambda)$, the diagonal coefficients $S_k$ of which are positive real numbers and V* is the conjugated transposed matrix of V, V being the matrix of spatial singular vectors of size $(N*M_\lambda)*(N*M_\lambda)$. An example of matrix S (302) is shown in FIG. 3A. A common convention is to arrange the values $S_k$ in the order of decreasing values.

According to what is illustrated in FIG. 3B, on the basis of singular value decomposition, the matrix A(r, t) can be expressed as a weighted sum of matrices the weighting coefficients of which are the diagonal coefficients $S_k$ of the 2D matrix of singular values:

$$A(r,t)=\sum_{k=1}^{N\times M_\lambda} S_k U_k(r) V_k(t)^* \quad \text{[Math. 70]}$$

In the above sum, each matrix $U_k(r)V_k(t)^*$defines a component corresponding to the singular value $S_k$. In order to perform a filtering, only certain components are kept and hence only certain matrices of the weighted sum are kept. When the values $S_k$ are arranged in the order of decreasing values, it is a question of selecting, during a step 330, values of minimum index a and maximum index b of the index k so that the matrix obtained after multispectral spatio-temporal filtering is:

$$A_{SVD}(r,t)=\sum_{k=a}^{b} S_k U_k(r) V_k(t)^* \quad \text{[Math. 71]}$$

The choice of the value of the minimum index a is important in that the index determines the efficiency and relevance of the filtering by determining which components of higher energy will be eliminated by filtering. The choice of the value of the maximum index b has a less sensitive impact on the filtering because same concerns the components of lower energy which include pure noise and, potentially, information embedded therein and can be chosen e.g. equal to a+100 or be comprised between a+1 and $N*M_\lambda$.

After elimination of the components corresponding to the singular values of highest energy, a transformation is performed during a step 340 which is inverse to the transformation performed during the step 310 from the matrix $A_{SVD}(r,t)$ for obtaining a temporal succession of filtered images denoted by:

$$A_{i,j}^{SVD}. \quad \text{[Math. 72]}$$

Figure 4A:
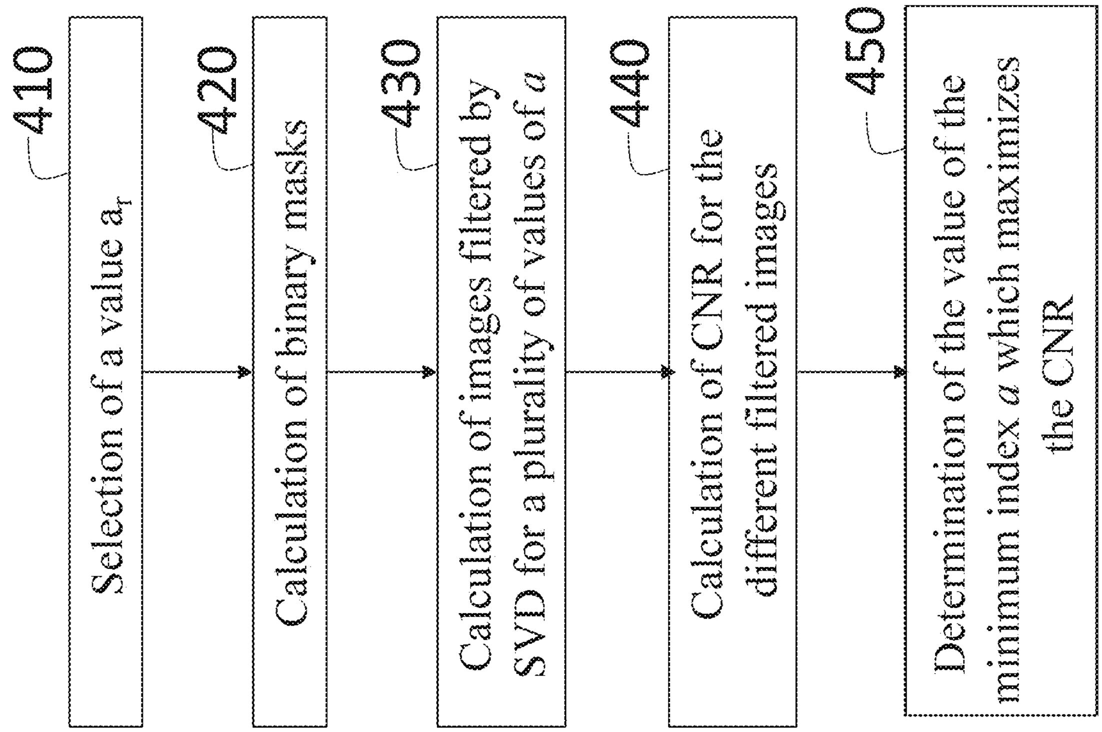
FIG. 4A represents a simplified flowchart of a singular value selection method that can be used during multispectral spatio-temporal filtering by singular value decomposition.
Figure 4B:
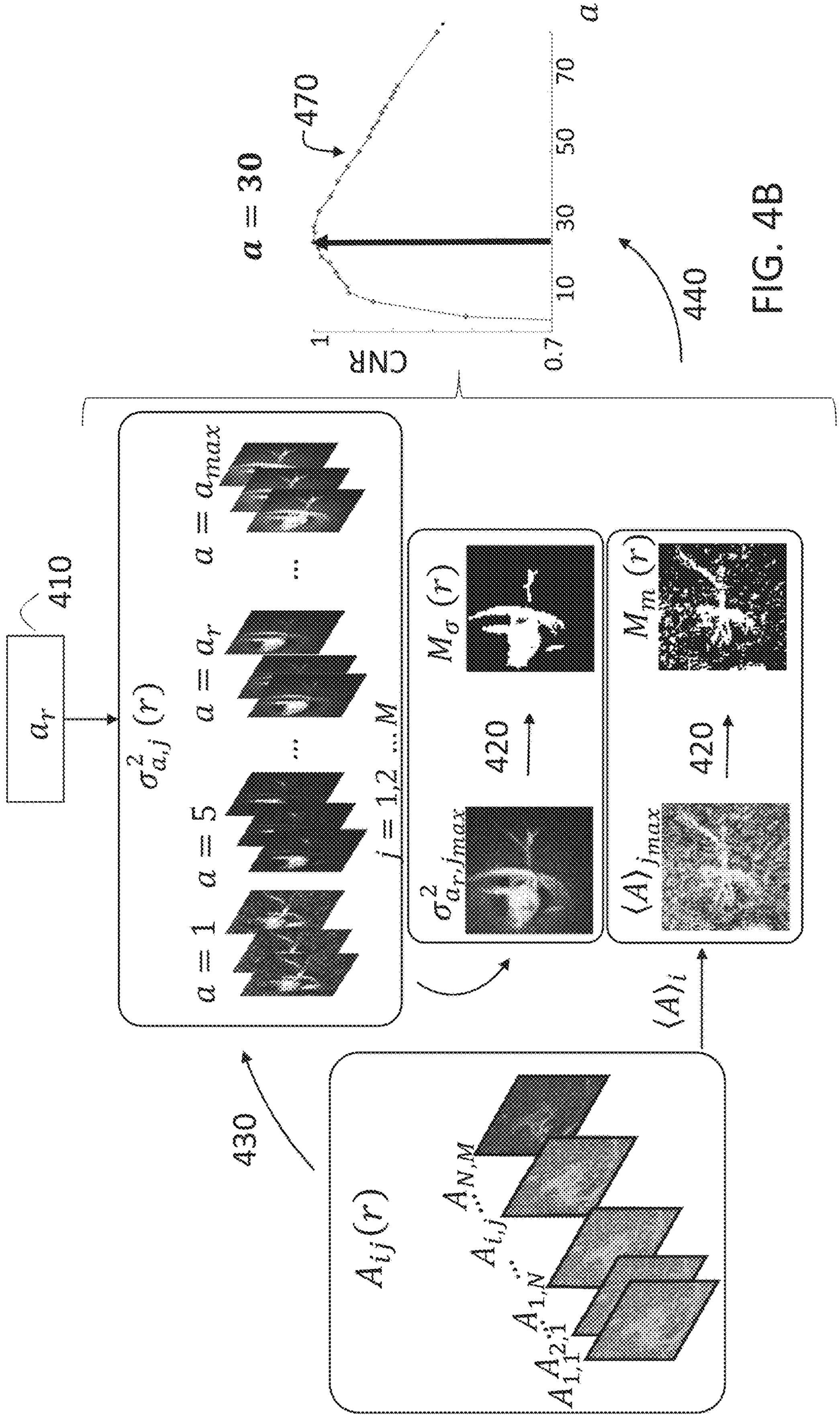
FIG. 4B illustrates aspects of a singular value selection method that can be used during multispectral spatio-temporal filtering by singular value decomposition.

FIGS. 4A-4B illustrate aspects of a method for selecting components to be removed during multispectral spatio-temporal filtering by SVD performed during the step 120.

FIG. 4A shows a simplified flowchart of a method for selecting the components to be eliminated during multispectral spatio-temporal filtering by SVD performed during the step 120, in particular the selection of the value of the minimum index a (also called lower limit) identifying which components will be eliminated by filtering.

The choice of the minimum index a can be delicate in that, by taking values of minimum index a that are too large, there is a risk of removing parts of the objects represented in an image. The method proposed herein makes it possible to select a minimum index value a in an automated way and without any risk of deleting parts of the objects represented in an image.

The method is based on an estimation of a Contrast-to-Noise Ratio (CNR) estimated for images filtered by SVD (without noise correction according to step 150A nor normalization by fluence according to the step 150B) for a plurality of values of the index a, and the value of the minimum index a which maximizes the contrast-to-noise ratio is determined.

The evaluation of the contrast-to-noise ratio is performed on the basis of a comparison between images filtered by SVD and masked images, in order to extract the structures that appear therein. The mask is obtained on the basis of the steps 410 and 420.

During the step 410, a reference value $a_r$ of the minimum index a is arbitrarily selected. For example, $a_r=0.03\times N\times M_\lambda=0.03\times 10\times 100=30$. Such value can be selected empirically from an analysis on a few representative samples.

A reference variance image at a single wavelength is then selected, denoted by:

$$\sigma^2_{a_r,j_{max}}(r) \quad \text{[Math. 73]}$$

for this reference value $a_r$ of the minimum index a and for a given wavelength $\lambda=\lambda_{jmax}$, which is e.g. the wavelength for which the SNR ("Signal to Noise Ratio") on the raw signals is the highest. The calculation of:

$$\sigma^2_{a_r,j_{max}}(r) \quad \text{[Math. 74]}$$

comprises the execution of the steps 120 (SVD) and 140 (filtered variance image) for images acquired for the wavelength of index $j_{max}$, but not the correction step 150.

During the step 420, 2 binary images used as binary masks, are calculated:

$M_\sigma$ is the binary mask calculated on the basis of the reference variance image:

$$\sigma^2_{a_r,jmax}(r) \quad \text{[Math. 75]}$$

based on a threshold value $th_a$;

$M_m$ is a binary mask calculated on the basis of the mean image:

$$\langle A\rangle_{jmax} \quad \text{[Math. 76]}$$

each pixel of which is calculated as the average of the pixels:

$$A_{i,jmax}(r) \quad \text{[Math. 77]}$$

on i, hence on all the images acquired for at least one given wavelength, chosen e.g. as being $\lambda=\lambda_{jmax}$. Another threshold value $th_m$ is used.

The determination of the threshold value $th_\sigma$ for obtaining the binary mask $M_\sigma$ can be performed on the basis of the following formula:

$$th_\sigma = \sigma_b^2 + \theta \times std_r(\sigma^2_{a_r,jmax}(r)) \quad \text{[Math. 78]}$$

where $$\sigma_b^2 \quad \text{[Math. 79]}$$

is to the spatio-temporal variance of the electronic noise, determined as e.g. described hereinabove for the step 150A.

$$std_r(\sigma^2_{a_r,jmax}(r)) \quad \text{[Math. 80]}$$

is the intra-image standard deviation calculated on the pixel distribution of the reference variance image;

$\theta$ is a weighting coefficient equal e.g. to 0.35, obtained empirically by making sure on a few examples, that the mask $M_\sigma$ obtained corresponds to the structure observable on the image:

$$\sigma^2_{a_r,jmax}(r) \quad \text{[Math. 81]}$$

The determination of the threshold value $th_m$ for obtaining the binary mask $M_m$ can be carried out on the basis of the following formula:

$$th_m = \langle\langle A\rangle_{jmax}\rangle_r + \theta \times std_r(\langle A\rangle_{jmax}) \quad \text{[Math. 82]}$$

where $$\langle\langle A\rangle_{jmax}\rangle_r \quad \text{[Math. 83]}$$

is the mean value of the pixels in the mean image denoted by:

$$\langle A\rangle_{jmax} \quad \text{[Math. 84]}$$

and $$std_r(\langle A\rangle_{jmax}) \quad \text{[Math. 85]}$$

is the intra-image standard deviation calculated on the pixel distribution of the mean image:

$$\langle A\rangle_{jmax} \quad \text{[Math. 86]}$$

The coefficient $\theta$ is the same as the coefficient used to obtain the mask $M_\sigma$.

A binary mask is used to distinguish in an image the background of the image from the rest, in particular of the object or objects represented in the image. In a known way, to calculate a binary mask on the basis of an image and a threshold value, it is determined whether the pixel value of the image is greater than (or equal to) the threshold: if the answer is yes, the value of the corresponding pixel in the binary mask is equal to 1 and if not, the value of the corresponding pixel in the binary mask is equal to 0.

The two binary masks obtained are used in the CNR formula, the calculation of which makes it possible to determine the minimum index a to be used for multispectral spatio-temporal filtering by SVD. The filtering is performed on all wavelengths and the minimum index a is the same for all wavelengths.

During a step 430, a plurality of values of the minimum index a are selected, e.g. from a set of predefined values such as 1 and 100, and the variance images are calculated at all wavelengths, denoted by:

$$\sigma^2_{a,j}(r) \quad \text{[Math. 87]}$$

for each value of the minimum index a.

During a step 440, a contrast-to-noise ratio value CNR(a) is calculated for each value of the minimum index a by using the two binary masks.

During a step 450, the value of the minimum index a for which the contrast-to-noise ratio CNR(a) is maximum is selected as the lower limit. The following variance image is used:

$$\sigma^2_{a,j}(r) \quad \text{[Math. 88]}$$

corresponding to the lower limit for carrying out the rest of the processings (in particular the steps 150 and 160 of the method described with reference to FIG. 1).

The Contrast-to-Noise Ratio (CNR) can be calculated in different ways on the basis of a binary mask that makes it possible to distinguish which pixels of the image are part of the image background and which pixels of the image are part of the object or objects represented in this image. In general, the contrast-to-noise ratio is the ratio between the contrast determined as the difference between the mean value of the pixels forming part of the object or objects and the mean value of the pixels forming part of the image background with respect to the fluctuation of the image background. The choice of the contrast-to-noise ratio as a criterion results in particular from the fact that, in order to visually detect pathologies in an image, the contrast thereof has to be greater than the fluctuation of the image background, and thus the contrast-to-noise ratio has to be greater than 1.

According to an exemplary embodiment, the contrast-to-noise ratio is calculated for each variance image at each wavelength:

$$\sigma_{a,j}^2(r) \quad \text{[Math. 90]}$$

obtained for the value of the minimum index a, then averaged over the wavelengths, as follows:

$$CNR(a) = \frac{1}{M}\sum_j^M \frac{\langle (M_\sigma - (M_\sigma \cap M_m)) \cdot \sigma_{a,j}^2 \rangle_r - \langle \overline{M_\sigma} \cdot \sigma_{a,j}^2 \rangle_r}{std_{\vec{r}}\left(\overline{M_\sigma} \cdot \sigma_{a,j}^2\right)} \quad \text{[Math. 91]}$$

where
M is the number of wavelengths $$\cap \quad \text{[Math. 92]}$$

is the operator representing the intersection of the two binary marks, the intersection corresponding to a logical AND function performed pixel by pixel between the two masks;

$$std_{\vec{r}} \quad \text{[Math. 93]}$$

is the intra-image standard deviation operation calculated on the distribution of pixels;

$$\overline{M_\sigma} \quad \text{[Math. 94]}$$

is the complement of the mask $M_\sigma$, i.e. $1-M_\sigma$ $$\overline{M_\sigma} \cdot \sigma_{a,j}^2 \quad \text{[Math. 95]}$$

is the term corresponding to the pixels belonging to the background of the image $$\langle \rangle_r \quad \text{[Math. 96]}$$

is the intra-image averaging operation calculated on the pixel distribution.

Such type of calculation formula is used, by means of the term $$M_\sigma \cap M_m \quad \text{[Math. 97]}$$

to eliminate in the calculation of the contrast-to-noise ratio the structures present both in the mean image and in the variance image. In the images acquired by a photoacoustic imaging technique, the mean value of the image is about 100 times larger than the rest, which would result in a very high CNR(a) value if the contrast due to the mean image value was not subtracted for the low values of the minimum index a. The mask used thereby ensures that the contrast increases when new structures appear. Thereby, in order to be able to compare in a relevant way the values of CNR(a) whatever the minimum index a, said specific calculation formula is used.

The example curve (470) of CNR(a) variations shown in the FIG. 4B shows that the contrast-to-noise ratio CNR(a) has a maximum for a value of the minimum index a comprised between 25 and 28. For another example, the value of the minimum index a is comprised between 33 and 35.

For the estimation of the electronic noise of the sensors used during the step 150A, a plurality of methods can be used.

According to a first noise estimation method, applicable in the case of a reconstructed image $$\sigma_j^2 \quad \text{[Math. 100]}$$

the electronic noise in the reconstructed image can be deduced from a spatial noise measurement of the real radio frequency signals.

$$\sigma_b^2 = 2N_{trans}\sigma_{b,RF}^2 \quad \text{[Math. 101]}$$

where $$N_{trans} \quad \text{[Math. 102]}$$

is the number of transducers used in the reconstruction $$\sigma_{b,RF}^2 \quad \text{[Math. 103]}$$

Is the variance of electronic noise on the measured radio frequency signals and is determined from raw signals obtained in the absence of a sample.

The factor 2 comes herein from the fact that signals with complex values are used for the reconstruction.

However, the estimation of $$\sigma_b^2 \quad \text{[Math. 104]}$$

can be corrected by considering that the multispectral spatio-temporal filtering by SVD removes an amount of noise equal to:

$$\Delta\sigma_{SVD}^2 = \frac{1}{NM_\lambda N_X N_Y N_Z}\sum_{k=b+1}^{NM_\lambda} S_k^2 \quad \text{[Math. 105]}$$

where b is the maximum index of the weighted sum of the matrices defining $$A_{SVD}(r, t) \quad \text{[Math. 106]}$$

$N_X N_Y N_Z$ is the number of pixels/voxels in the reconstructed image and $S_k$ the singular values obtained by the SVD.

It has been observed that singular values representing the noise, present in the expression of:

$$\sigma^2_{SVD} \quad \text{[Math. 107]}$$

are stationary with respect to wavelengths.

Finally, the residual electronic noise after SVD to be subtracted during the step 150A from the variance images in order to obtain corrected variance images will be:

$$\sigma^2_{b,SVD} = 2N_{trans}\sigma^2_{b,RF} - \Delta\sigma^2_{SVD} \quad \text{[Math. 108]}$$

According to a second noise estimation method, if the noise does not follow said law, it is possible to perform an alternative correction, e.g. by minimizing the norm L2 of the reconstructed image:

$$\sigma^2_j \quad \text{[Math. 110]}$$

subject to the subtraction of a constant:

$$\sigma_b = \arg\min_Q \sum_{j=1}^{M_\lambda} \left\|\sigma^2_j(r) - Q^2\right\| \quad \text{[Math. 111]}$$

The value of the constant $$Q^2 \quad \text{[Math. 112]}$$

minimizing the norm can be used for calculating the value:

$$\sigma^2_{b,SVD} \quad \text{[Math. 113]}$$

to be subtracted from $$\sigma^2_j(r) \quad \text{[Math. 115]}$$

Other methods for estimating the level of noise can be used.

The photoacoustic image processing method described in the present document was applied to volume images acquired in the chicken embryo and we find values close to oxygenation rate with conventional photoacoustic spectroscopy based on a mean image in visible structures.

Figure 5A:
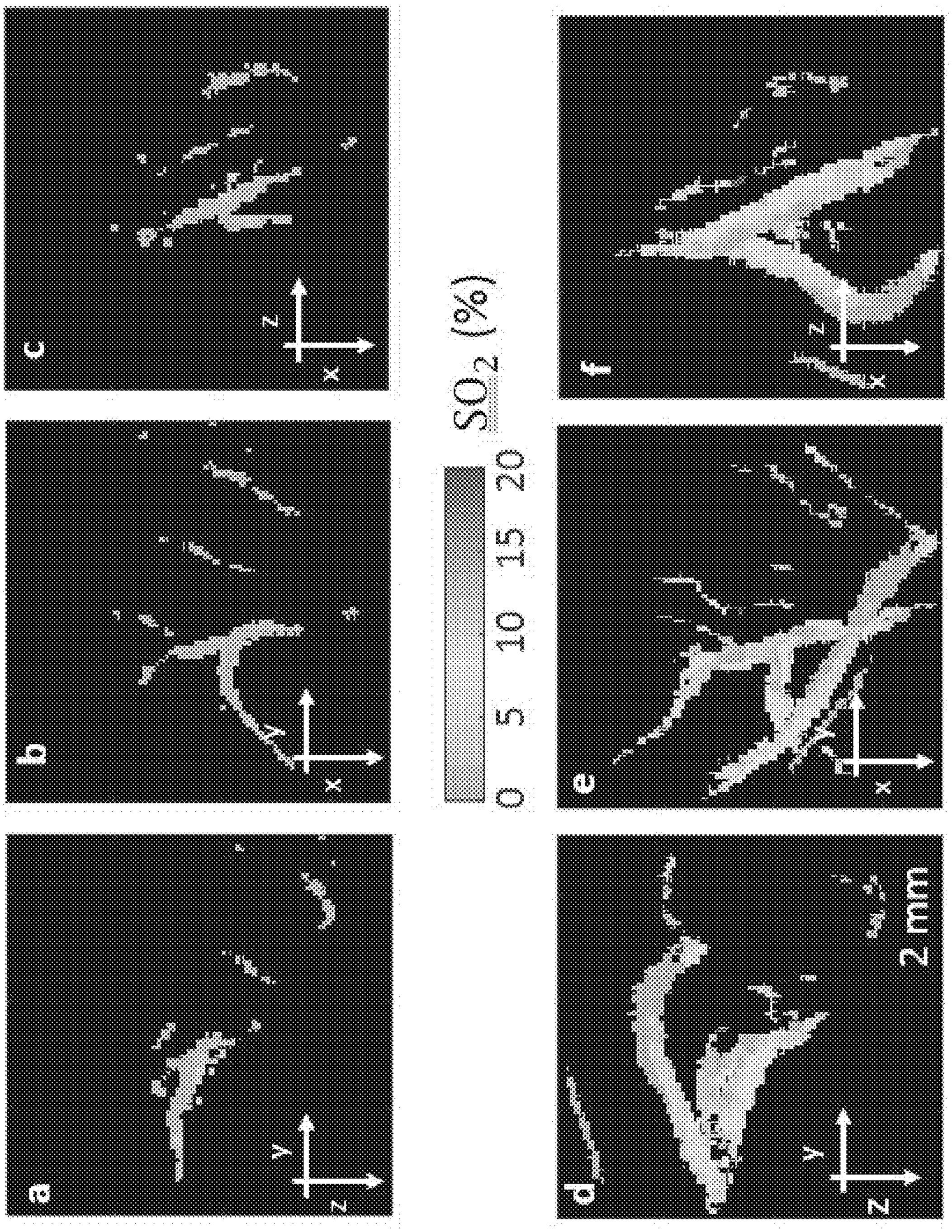
FIG. 5A shows two examples of oxygenation images obtained by a method for processing images acquired according to the present description and acquired according to a conventional method.
Figure 5B:
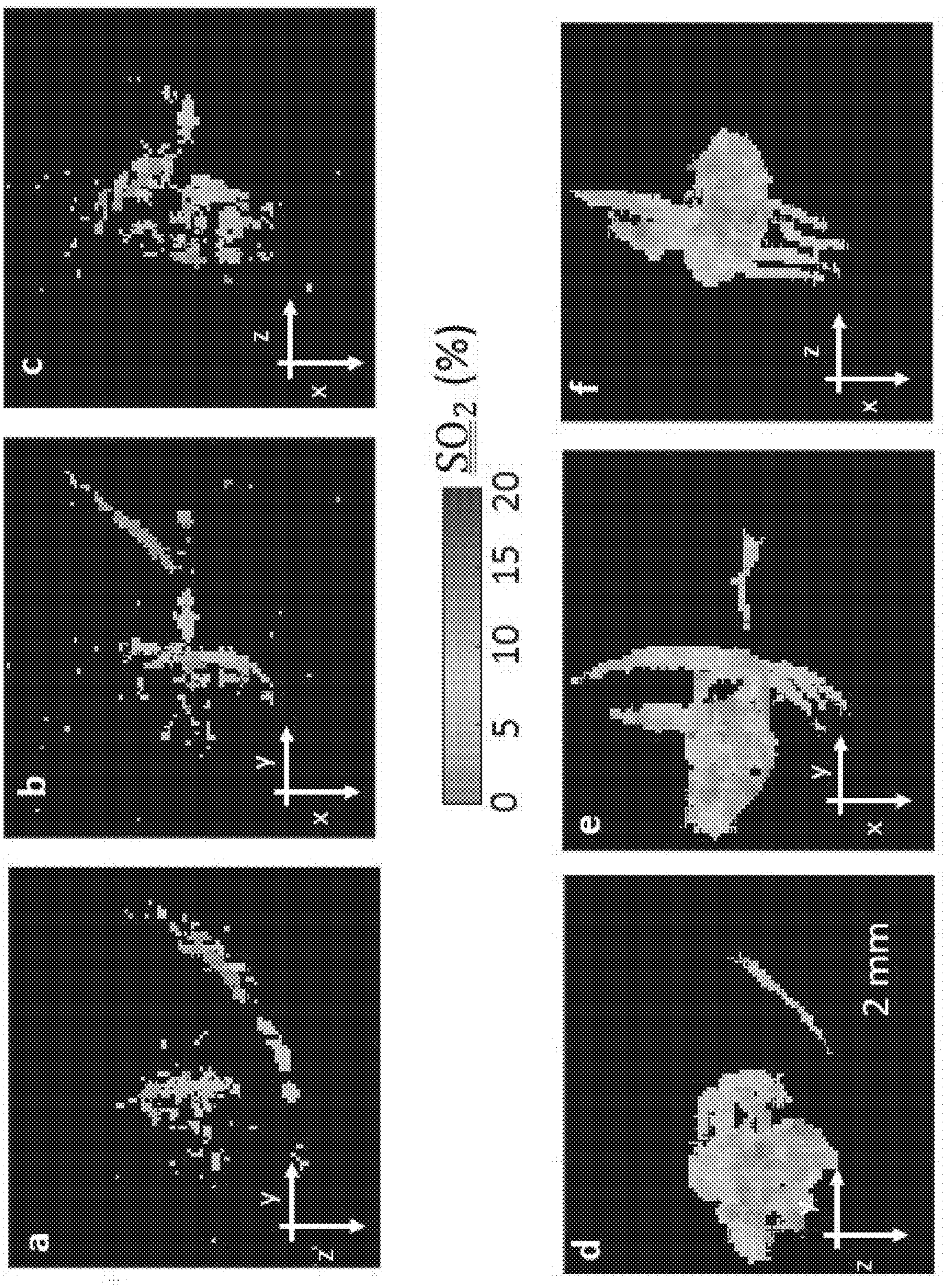
FIG. 5B shows two examples of oxygenation images obtained by a method for processing images acquired according to the present description and acquired according to a conventional method.

FIGS. 5A-B show the improvement of the visibility of certain elements of the biological tissue by the method described in the present document in the case of the application thereof to the imaging of oxygenation of blood vessels. Two examples are shown. In both examples (FIG. 5A and FIG. 5B), the first line corresponds from left to right to an oxygenation image obtained from the average photoacoustic image m, along three projection planes YZ (a), XY (b) and XZ (c). The oxygenation images have a limited visibility. The oxygenation 3D image obtained from the absorption fluctuations imaging is shown on the second line, with a projection according to the same planes YZ (d), XY (e) and XZ (f) where many more structures can be seen than with a conventional photoacoustic imaging technique.

In FIG. 5A, the imaged zone corresponds to the chorioallantoic membrane. The technique of absorption fluctuations imaging (FIG. 5A, images d,e,f) makes it possible to extend the oxygenation measurement to many more vessels since some did not appear on the conventional image (FIG. 5A, images a,b,c) because of the orientation or size thereof.

In FIG. 5B, the imaged area corresponds to the heart of the chicken embryo. The fluctuation technique (FIG. 5B, images d,e,f) makes it possible to extend the oxygenation measurement to the whole organ as well as to the outgoing vessels while very little information appears on the conventional image (FIG. 5B, images a,b,c) as a discontinuous pixel distribution.

In the case where the medium is transparent (as in the case of the chicken embryo with vascularization surrounded by a clear medium), it is not necessary to correct the spectral coloration due to the use of a plurality of wavelengths by the biological tissue.

The blood flow oxygenation imaging method that has been described herein pushes the limitations of conventional detectors with minor hardware modifications: in order to extract the fluctuation of interest and to perform post-processing as described herein, it is enough to acquire enough images (typically at least 50).

The functions, motors, principle diagrams, flow diagrams, state transition diagrams and/or flowcharts presented in the present document represent conceptual views of illustrative circuits implementing the principles of the invention. Similarly, all flowcharts, flow diagrams, state transition diagrams, pseudo-codes and other represent various aspects of the method which can be implemented essentially by computer program instructions stored on a computer-readable medium and thereby be implemented by a processor or a device including a processor, whether or not the processor or the device is explicitly represented.

According to one embodiment, one or a plurality of all the steps of a photoacoustic image processing method are implemented by a software or computer program.

The present description thereby relates to a computer program which can be executed by a data processor, the computer program including computer program instructions for controlling the execution by a device of one or a plurality of or all of the steps of a photoacoustic image processing method according to any of the embodiments described in the present document. The computer program instructions are intended e.g. to be stored in a memory of a device, loaded and then executed by a processor of this device.

The computer program can use any programming language, and may be in the form of source code, object code, or of intermediate code between source code and object code, such as in a partially compiled form, or any other desirable form.

The device can be implemented by one or a plurality of physically distinct machines and, overall, has the architecture of a computer, including components of such an architecture: data memory or memories, processor(s), communication bus, hardware interface(s) for connecting this computing device to a network or another equipment, user interface(s), etc.

The present description further relates to an information medium readable by a data processor and including instructions of a computer program as mentioned hereinabove. The information medium can be any entity or device apt to store the program.

The information medium can be any hardware means, entity or device apt to store a signal. For example, the medium can include a storage means, such as a ROM or RAM memory, e.g. a CD ROM disk or a magnetic recording means, a computer hard disk, optical storage media, flash memory devices and/or other tangible machine-readable media for storing information.

The term "computer-readable medium" can include, but is not limited to, portable or fixed storage devices, optical storage devices and various other media apt to store, contain or transport instructions and/or data.

It can be a computer storage medium and/or communication media, or more generally any medium that facilitates the transfer of a computer program from one place to another.

Examples of computer-readable media include, but are not limited to, a flash drive or other flash memory devices (e.g., memory keys, memory sticks, a USB key drive), a CD-ROM or other optical storage, a DVD, magnetic disk storage or other magnetic storage devices, a solid state memory, a memory chip, a RAM, a ROM, an EEPROM, smart cards, a relational database management system, a company data management system, etc.

The information medium can be a medium transmissible in the form of a carrier wave such as an electromagnetic signal (electrical, radio or optical signal), which can be carried via appropriate wired or non-wired transmission means: electrical or optical cable, radio or infrared link, or by other means.

The term "processor" can e.g. refer to any microprocessor, microcontroller, controller, integrated circuit or central processing unit (CPU) comprising one or a plurality of processing units or one or a plurality of processing kernels based on hardware. Moreover, the term "processor" should not be interpreted as referring exclusively to hardware apt to execute computer program instructions but can refer e.g. to a digital signal processor (DSP), a network processor, an application specific integrated circuit (ASIC), a field programmable gate array (FPGA), or other circuit whether programmable or not, either specific or not specific. The term "processor" can also correspond to a combination of a plurality of exemplary embodiments mentioned herein.

The present invention relates to a photoacoustic image processing device comprising, at least one data memory comprising program code instructions, at least one data processor, the data processor being configured so that, when the program code instructions are executed by the data processor, the photoacoustic image processing device executes one or a plurality of or all of the steps of a photoacoustic image processing method according to any of the embodiments described herein.

In one embodiment, the photoacoustic image processing device comprises:

data storage means, e.g. one or a plurality of memories, for storing computer program instructions designed to control the execution of one or a plurality of or all of the steps of a photoacoustic image processing method according to any of the embodiments described in the present document;

data processing means, in particular a data processor, configured to execute the computer program instructions in order to implement one or a plurality of or all of the steps of a photoacoustic image processing method according to any of the embodiments described in the present document.

More generally, the photoacoustic image processing device comprises means for implementing one or a plurality of or all of the steps of a photoacoustic image processing method according to any of the embodiments described in the present document. The means comprise e.g. software and/or hardware means.

The invention claimed is:

1. A method for improving visibility in photoacoustic images, comprising acquiring by photoacoustic imaging a temporal succession of images of a sample acquired by a photoacoustic imaging system for Ma excitation pulse wavelengths with N images acquired per wavelength;

multispectral spatio-temporal filtering by singular value decomposition applied to all the N*MA images acquired so as to obtain N*Ma filtered images;

for each wavelength, calculating a filtered variance image from the N filtered images, one pixel of coordinate r in the filtered variance image being equal to the variance of the distribution of pixel values of the same coordinate r in the filtered images obtained for that wavelength;

for each wavelength, correcting the filtered variance image by subtracting a variance of the residual electronic noise after the multispectral spatio-temporal filtering produced by the ultrasonic wave sensors of the photoacoustic imaging system to obtain a visibility-improved image.

2. The method according to claim 1, wherein the method comprises, for each wavelength, a determination of a corrected image of fluctuations, each pixel of the corrected image of fluctuations being equal to the square root of the corresponding pixel of the corrected variance image obtained by the subtraction for the wavelength considered.

3. The method according to claim 1, further comprising estimating the variance of the residual electronic noise produced by the ultrasonic wave sensors on the images, the variance of the residual electronic noise produced by the ultrasonic wave sensors on the images being estimated as a function of a variance of the electronic noise produced in the photoacoustic signals acquired in the absence of a sample corrected by an amount of noise eliminated by the multispectral spatio-temporal filtering by decomposition into singular values, the amount of noise eliminated being estimated based on the singular values corresponding to the lowest energy components removed by the multispectral spatio-temporal filtering by singular decomposition.

4. The method according to claim 1, comprising for each wavelength considered, normalizing the image of fluctuations corrected by a function of the laser pulse fluence of the photoacoustic imaging system, so as to obtain an image of absorption fluctuations representative of the absorption fluctuations due to the sample.

5. The method according to claim 4, the method comprising calculating an image of the oxygen saturation rate from at least two images of absorption fluctuations obtained for at least two corresponding wavelengths.

6. The method according to claim 5, wherein the calculation of an image of the oxygen saturation rate is performed based on a model expressing, for each pixel of coordinate r, a relation between a total hemoglobin concentration, an oxygen saturation rate and the value at pixel r of the image of absorption fluctuations.

7. The method according to claim 1, wherein the multispectral spatio-temporal filtering by singular value decomposition comprises selecting the components corresponding to the highest energy singular values to be removed and removing selected components, the selection being made by choosing, from a set of index values, an index identifying the first component to be kept for which a contrast-to-noise ratio is maximum, the contrast-to-noise ratio determined for an index being determined for filtered variance images calculated by multispectral spatio-temporal filtering by decomposition into singular values applying the index in order to identify the first component to be kept.

8. The method according to claim 7, wherein the contrast-to-noise ratio is determined by eliminating the contrast due to the mean value of the images acquired for at least one wavelength.

9. A photoacoustic image processing device comprising at least one data memory comprising program code instructions, at least one data processor, the data processor being configured to, when the program code instructions are executed by the data processor, make the photoacoustic image processing device execute a method according to claim 1.

10. A non transitory computer-readable storage medium including computer program instructions which, when executed by a processor, execute a method according to claim 1.

* * * * *